United States Patent [19]

Tanaka et al.

[11] Patent Number: 5,356,805
[45] Date of Patent: Oct. 18, 1994

[54] GAMMA-POLYGLUTAMATE HYDROLASE

[75] Inventors: Toshio Tanaka; Makoto Taniguchi, both of Osaka; Osamu Hiruta; Kazumichi Uotani, both of Kanagawa, all of Japan

[73] Assignee: Meiji Seika Kaisha, Ltd., Tokyo, Japan

[21] Appl. No.: 25,344

[22] Filed: Mar. 3, 1993

[30] Foreign Application Priority Data

Mar. 3, 1992 [JP] Japan ................................. 4-045517
Jan. 25, 1993 [JP] Japan ................................. 5-009665

[51] Int. Cl.$^5$ ........................ C12N 9/58; C12N 9/14; C12N 9/52
[52] U.S. Cl. ................................. 435/223; 435/110; 435/195; 435/212; 435/220; 435/911; 435/254.1
[58] Field of Search .............. 435/223, 212, 220, 195, 435/110, 254.1, 911

[56] References Cited

U.S. PATENT DOCUMENTS

| | | | |
|---|---|---|---|
| 3,648,850 | 2/1972 | Ichishima et al. | 435/225 |
| 3,957,581 | 5/1976 | Tobe et al. | 435/223 |
| 4,339,534 | 7/1982 | Johansen et al. | 435/68.1 |
| 4,415,667 | 11/1983 | Koide et al. | 435/212 |
| 4,532,207 | 7/1985 | Brewer et al. | 435/68.1 |

Primary Examiner—Herbert J. Lilling
Attorney, Agent, or Firm—Sughrue, Mion, Zinn, Macpeak & Seas

[57] ABSTRACT

An enzyme produced by a microorganism belonging to the genus Myrothecium hydrolyzes γ-polyglutamic acid with an endo action to produce oligoglutamic acid consisting of 2 to 4 glutamic acid residues.

1 Claim, No Drawings

GAMMA-POLYGLUTAMATE HYDROLASE

FIELD OF THE INVENTION

The present invention relates to a novel γ-polyglutamate hydrolase produced by a microorganism belonging to the genus Myrothecium of Fungi Imperfecti and to a process for the production of the enzyme.

BACKGROUND OF THE INVENTION

α-Polyglutamic acid has been used as materials of artificial leather and the like, while γ-polyglutamic acid has been known as a component of viscous materials of a Japanese fermented soybean food called natto. In recent years, attempts have been made to produce γ-polyglutamic acid as a new material by means of a large scale culturing. The present inventors have developed a process for the economical production of γ-polyglutamic acid in a large scale using a bacterium belonging to the genus Bacillus (JP-A-1-174397; the term "JP-A" as used herein means an "unexamined published Japanese patent application").

The γ-polyglutamic acid produced by culturing a bacterium belonging to the genus Bacillus has a molecular weight of more than 1,000,000. It is useful as a viscosity-adding agent but not applicable to other use because of its too high viscosity. Polyglutamate hydrolase produced by *Micromonospora melanosporea* IFO 12515 (T. Muro et al., *Agr. Biol. Chem.*, 54(4), 1065, (1990)) and γ-glutamyl transpeptidase are known as enzymes which reduces molecular weight of γ-polyglutamic acid. The substrate of the former enzyme is α-polyglutamic acid and that of the latter is γ-polyglutamic acid. Both enzymes act as exo-acting enzymes by cleaving and liberating glutamic acid consecutively from the end of the polyglutamic acid chain. To date, no endo-acting enzyme which hydrolyzes γ-polyglutamic acid has been known. Thus, it has been desired to develop an enzyme which can reduce molecular weight of γ-polyglutamic acid by hydrolyzing it with an endo action.

It is reported that γ-polyglutamic acid produced by fermentation is considered a mixture of a homopeptide composed of L-glutamic acid, namely poly-L-glutamic acid, and a homopeptide composed of D-glutamic acid, namely poly-D-glutamic acid (S. Murao, *Kohbunshi*, 16(188), 1204–1212 (1969)).

SUMMARY OF THE INVENTION

In order to overcome the above-mentioned problems, the present inventors have conducted intensive studies on screening of a microorganism from various natural sources, which could produce a γ-polyglutamate hydrolase. As a result, the present inventors have found that a microbial strain (TM-4222) isolated from a soil sample was able to produce γ-polyglutamate hydrolase in a culture medium. Also, the present inventors have found that γ-oligo-L-glutamic acid and γ-poly-D-glutamic acid can be produced efficiently using this enzyme.

Accordingly, an object of the present invention is to provide a novel γ-polyglutamate hydrolase which specifically hydrolyzes γ-poly-L-glutamic acid with an endo action.

Another object of the present invention is to provide a process for the production of γ-polyglutamate hydrolase which comprises culturing a microorganism belonging to the genus Myrothecium and recovering the enzyme from the resulting culture.

DETAILED DESCRIPTION OF THE INVENTION

Mycological properties of the strain TM-4222 to be used in the present invention are as follows.

Growth characteristics

When cultured at 25° C. for 2 weeks, it forms a colony having a diameter of; 35 to 40 mm on a potato-dextrose agar medium, 50 to 60 mm on an oatmeal agar medium, 25 to 30 mm on a malt extract agar medium, or 35 to 40 mm on a Czapeck-Dox agar medium. In each case of the above culture media, a viscous cluster of olive colored conidia are formed on white velvety or woolly substrate mycelia. In the case of the malt extract and Czapeck-Dox agar media, the formed colony is sometimes partly covered with white and fluffy aerial mycelia. Backside of the colony is pale yellow in every case of the media. This strain does not grow at 37° C.

Morphological characteristics

The mycelium is achromatic and smooth on the surface and possessed of septa. The conidium is a phialospore type, each phialospore being cylindrical to elliptical in shape and 6–7×2–3 μm in size. Two to 5 phialides grow in a verticillate form, each phialide being columnar in shape with slight thinning toward its tip, achromatic and 10–15×2–2.5 μm in size.

By referring these mycological properties to *Kingaku Zukan* (a picture book on mycology; Kodan-sha Scientific, 1978), TM-4222 was identified as a strain belonging to the genus Myrothecium (Myrothecium sp.) of the class Fungi Imperfecti. This strain has been deposited at National Institute of Bioscience and Human-Technology, Agency of Industrial Science and Technology, of 1–3, Higashi 1-chome, Tsukuba-shi, Ibaraki, Japan, as the accession No. FERM BP-4161 in accordance with the Budapest Treaty.

Enzymological and physicochemical properties of the γ-polyglutamate hydrolase produced by this strain are described in the following.

1. Action

This enzyme specifically hydrolyzes γ-poly-L-glutamic acid with an endo action and liberates γ-oligo-L-glutamic acid which consists of 2 to 4 γ-glutamic acid residues.

2. Substrate specificity

It hydrolyzes γ-bonds of γ-poly-L-glutamic acid and liberates oligo-L-glutamic acid but does not act on α-bonds of α-polyglutamic acid. Also, it does not hydrolyze γ-bonds of glutamylglutamic acid, glutathione and γ-glutamylnaphthylamide which is a synthetic substrate of γ-glutamyl transpeptidase (γ-GTP). This enzyme, therefore, shows an endo action pattern.

3. Optimum pH and stable pH range

It has an optimum pH of 5.0 and a stable pH range of from 4.0 to 6.0.

4. Optimum reaction temperature and stable temperature range

It has an optimum reaction temperature of 37° C. and is stable up to 40° C. when treated at pH 5.0 for 1 hour.

5. Molecular weight

It has a molecular weight, measured by gel filtration, of about 68,000.

6. Measurement of γ-polyglutamate hydrolase activity (1) Viscosity method

A reaction mixture consisting of 4 ml of 2% γ-polyglutamic acid solution (pH 5.0), 2 ml of 0.4M acetate buffer (pH 5.0) and 2 ml of an enzyme solution was put into an Ostwald viscometer and incubated at 37° C. for 30 minutes. One unit (U) of the activity was defined as the amount of enzyme decreasing viscosity of γ-polyglutamic acid at a rate of 1 second per 1 minute under these reaction conditions. In this instance, the amount of enzyme was proportional to the decrease in viscosity within the range of from 0.05 U to 0.33 U under these reaction conditions.

(2) Ninhydrin reaction method

A 1 ml portion of a reaction mixture having the same composition as described above was incubated at 37° C. for 30 minutes, and the reaction was stopped by adding 1.2 ml of a methyl cellosolve solution for ninhydrin color development, followed by the measurement of the amount of free amino groups by the ninhydrin reaction. One unit of the activity was defined as the amount of enzyme forming free amino groups equivalent to 1 μmol L-glutamic acid per 1 minute under these reaction conditions. In this instance, the enzyme activity was measurable within the range of from 0.004 U to 0.033 U.

Any synthetic or natural medium can be used in the present invention as long as it contains nutrients including carbon sources, nitrogen sources, inorganic substances and other nutrients.

Usable as a carbon source are glucose, sucrose, glycerol, xylose, fructose, maltose, molasses, starch hydrolysis products and the like. Usable as a nitrogen source are inorganic sources such as nitrate and an ammonium salt and organic sources such as peptone, polypeptone, yeast extract, corn steep liquor and casein hydrolisys products. Examples of the inorganic substances include potassium phosphate, magnesium sulfate, manganese, iron and the like.

The cultivation of the microorganism is carried out at 20° to 40° C., preferably 25° to 30° C., under the aerobic conditions, for example, with shaking or aerobic agitation. The medium is adjusted to pH 5 to 9, preferably pH 6 to 8 with sodium hydroxide, potassium hydroxide, hydrochloric acid, sulfuric acid and the like. The product, γ-polyglutamate hydrolase, is accumulated in the culture mainly extracellularly within 5 to 8-day cultivation.

When the enzyme of the present invention is allowed to react with the currently available γ-polyglutamic acid which is a mixture of a D-form polymer and an L-form polymer, the L-form polymer is degraded into an L-glutamic acid oligomer consisting of 2 to 4 L-glutamic acid residues linked through γ-bonds. On the other hand, the D-form polymer is not hydrolyzed and remains as it is.

The enzyme reaction can carried out by allowing γ-polyglutamic acid to react with γ-polyglutamate hydrolase of the present invention in an aqueous solution of pH 4 to 6 at 35° to 39° C. The substrate, γ-polyglutamic acid, is used in a considerably excess amount based on the enzyme. The reaction products, γ-poly-D-glutamic acid and γ-oligo-L-glutamic acid, can be recovered and purified from the reaction mixture by the known methods including precipitation with ammonium sulfate, dialysis, column chromatography using DEAE-Sephadex, etc., affinity chromatography and the like.

Thus, γ-polyglutamate hydrolase of the present invention can decrease viscosity of γ-polyglutamic acid rapidly without liberating free glutamic acid and produce γ-oligo-L-glutamic acid and γ-poly-D-glutamic acid.

The enzyme of the present invention is usable in the production of:

(1) D-glutamic acid polymer which has different viscosity characteristics from γ-polyglutamic acid and can be applied to food articles and new materials;

(2) D-glutamic acid obtained by chemical hydrolysis of the D-form polymer, which is very expensive in comparison with L-glutamic acid and can be used as a reagent; and (3) L-glutamic acid oligomer which is found in the mammalian brain and is expected to exert a physiological function on the central nerve system.

The following examples are provided to further illustrate the present invention, but are not to be construed to limit the scope of the present invention.

EXAMPLE 1

(1) Myrothecium sp. TM-4222 (FERM BP-4161) was inoculated into modified Czapeck-Dox medium (3.0% sucrose, 0.2% $NaNO_3$, 0.1% $KH_2PO_4$, 0.05% $MgSO_4.7H_2O$, 0.001% $FeSO_4.7H_2O$, pH 6.0) supplemented with 0.5% yeast extracts but containing no γ-polyglutamic acid to give a cell density of 20 to 50 g/l (dry basis) and cultured at 25° C. for 7 days using a jar fermentor to allow it to produce γ-polyglutamate hydrolase. The same productivity was observed when glycerol, potato starch or dextrin was used as the carbon source or polypeptone, casein or casamino acid was used as the nitrogen source. Also, the enzyme activity obtained when 0.5% of γ-polyglutamic acid was added to the medium was 1.5 to 2 times as high as that in the case of adding no γ-polyglutamic acid.

(2) A 2 liter portion of the culture filtrate obtained in the above step (1) was adjusted to pH 4.0 with acetic acid and applied to a column (4.4×18 cm) packed with Bio-Rex 70 (Bio-Rad Laboratories, Inc.) which had been equilibrated in advance with 0.05M acetate buffer (pH 4.0). After washing the column thoroughly with the same buffer, the adsorbed enzyme was eluted by a density gradient elution using 400 ml of 0.05M acetate buffer (pH 4.0) and 400 ml of 1.0M acetate buffer (pH 6.0), followed by further elution with the latter buffer. The eluate was collected in 10 ml fractions. The elution pattern of protein was prepared by measuring the absorbance at 280 nm, and the elution pattern of γ-polyglutamate hydrolase was determined by the ninhydrin reaction method (these detection methods were applied to the chromatographic procedure carried out in the following). The γ-polyglutamate hydrolase activity was found in fraction Nos. 125 to 160 which had been eluted using the 1.0M acetate buffer after completion of the density gradient elution.

(3) The active fractions recovered in the above step (2) were pooled, dialyzed against 0.05M acetate buffer (pH 5.0) and then applied to a column (2.2×5.0 cm) packed with AF-Blue Toyopearl (Tosoh Corp.) which had been equilibrated in advance with the same buffer. After washing the column with the same buffer to remove non-adsorved components, the adsorbed enzyme was eluted with the same buffer further supplemented with 0.2M sodium chloride.

(4) Affinity chromatography was carried out using a column packed with a γ-polyglutamic acid-coupled Sepharose 4B.

The γ-polyglutamic acid-coupled Sepharose 4B was prepared in the following manner. A 5 ml portion of EAH-Sepharose 4B (Sigma Chemical Co.) was put on a glass filter and washed with 80 ml of 0.5M sodium chloride per 1 ml of the sedimentation gel. Separately, γ-polyglutamic acid equivalent to 0.5 mmol of L-glutamic acid was dissolved in 10 ml of distilled water, and the resulting solution was adjusted to pH 4.5 with 1N sodium hydroxide. Further, 50 mg of 1-ethyl-3-(3-diethylaminopropyl) carbodiimide was dissolved in 5 ml of distilled water, and the resulting solution was adjusted to pH 4.5 with 1N sodium hydroxide. 5 ml of the thus washed gel, 10 ml of the γ-glutamic acid (ligand) solution and 5 ml of the carbodiimide solution were mixed and gently shaken overnight at room temperature to effect the coupling reaction.

The active fraction obtained in the above step (3) was dialyzed against 0.05M acetate buffer (pH 4.0) and then applied to a column (1.8×5.0 cm) packed with the γ-polyglutamic acid-coupled Sepharose 4B as prepared above. After washing the column with the same buffer, the adsorbed enzyme was eluted by a pH gradient using 100 ml of the same buffer and 100 ml of 0.05M acetate buffer (pH 6.0), followed by further washing with the latter buffer. Most of the protein components were found in the passed-through fractions, while active fractions were obtained as a single peak after completion of the pH gradient. Fraction nos. 86 to 90 were pooled. In the first half of the fractions proteinous impurities were found and in the latter half fractions the absorbance at 280 nm was hardly detectable.

(5) The thus pooled active fractions were concentrated by ultrafiltration and then passed through a column (3.9×64.5 cm) packed with Sephacryl S-300 (Pharmacia) which had been equilibrated in advance with 50 mM acetate buffer (pH 5.0) containing 150 mM sodium chloride. When the eluate was collected in 10 ml fractions, the enzyme activity was found in fraction Nos. 46 to 50. Specific activity of the thus purified enzyme was found to be 362 U/mg protein by the ninhydrin reaction method.

EXAMPLE 2

(1) The culture supernatent obtained in the same manner as in Example 1 was desalted by ultrafiltration and lyophilized to obtain crude γ-polyglutamate hydrolase. 0.5 g of the thus obtained enzyme powder was added to 100 ml of 100 mM acetate buffer (pH 4.5) containing 1.0% of γ-polyglutamic acid (molecular weight, 1,240,000) which was produced by the method described in JP-A-174397 using *Bacillus subtilis* F-2-01 and the mixture was incubated in a water bath maintained at 30° C. for 18 hours to effect the hydrolyzing reaction. After completion of the reaction, 1 ml of 10% trichloroacetic acid solution was added to the resulting reaction mixture and the precipitate thus formed was removed by filtration with suction. Thereafter, the thus obtained filtrate was subjected to ultrafiltration using a membrane having a molecular weight cutoff of 10,000 to thereby divide the reaction products into a fraction containing the D-form polymer and another fraction containing low molecular weight hydrolyzation products of the L-form polymer.

(2) The D-form polymer fraction was washed thoroughly with water using the aforementioned ultrafiltration membrane to remove low molecular weight impurities and then freeze-dried to obtain about 200 mg of white powder.

(3) The L-form low molecular weight fraction was applied to a column (2.5×25 cm) packed with DiaIon UBK-520G (H+) (Mitsubishi Kasei Corp.). After washing the column thoroughly with deionized water, the adsorbed product was eluted with 0.1N hydrochloric acid. The eluate was concentrated under a reduced pressure with adding water to remove hycrochloric acid. Thus, about 300 mg of white powder was obtained.

(4) The D-form polymer powder obtained in the above step (2) was subjected to GPC analysis to find a peak molecular weight of about 200,000. The powder was also subjected to hydrolysis with hydrochloric acid and the resulting hydrolysis product was analyzed by optical resolution liquid chromatography. The results revealed that the hydrolysis product was D-glutamic acid.

(5) The L-form polymer powder obtained in the above step (3) was subjected to amino acid analysis and hydrolysis with hydrochloric acid followed by optical resolution liquid chromatography to find that the powder was a mixture of dimer to tetramer of L-glutamic acid.

While the invention has been described in detail and with reference to specific examples thereof, it will be apparent to one skilled in the art that various changes and modifications can be made therein without departing from the spirit and scope thereof.

What is claimed is:

1. An isolated γ-polyglutamate hydrolase which has the following physicochemical properties:
   (1) it hydrolyzes γ-polyglutamic acid with an endo action and liberates γ-oligoglutamic acid;
   (2) it hydrolyzes γ-polyglutamic acid and liberates oligoglutamic acid but does not act on α-polyglutamic acid, and does not hydrolyze γ-glutamylglutamic acid, glutathione and γ-glutamylnaphthylamide which is a synthetic substrate of γ-glutamyl transpeptidase (γ-GTP);
   (3) it has an optimum pH of 5.0 and a stable pH range of from 4.0 to 6.0;
   (4) it has an optimum reaction temperature of 37° C. and is stable up to 40° C. at pH 5.0 for 1 hour; and
   (5) it has a molecular weight, measured by gel filtration, of about 68,000.

* * * * *